(12) United States Patent
Heil, Jr. et al.

(10) Patent No.: US 6,168,801 B1
(45) Date of Patent: Jan. 2, 2001

(54) CONTROLLED RELEASE DRUG DELIVERY

(75) Inventors: Ronald W. Heil, Jr., Roseville; Bruce H. KenKnight, Maple Grove, both of MN (US)

(73) Assignee: Cardiac Pacemakers, Inc., St. Paul, MN (US)

( * ) Notice: Under 35 U.S.C. 154(b), the term of this patent shall be extended for 0 days.

(21) Appl. No.: 09/272,428

(22) Filed: Mar. 19, 1999

Related U.S. Application Data

(63) Continuation of application No. 09/150,399, filed on Sep. 9, 1998, now abandoned.

(51) Int. Cl.[7] ....................................... A61F 2/02

(52) U.S. Cl. .......................... 424/426; 424/424; 424/425

(58) Field of Search ................... 424/424, 425, 424/426; 514/772.3

(56) References Cited

U.S. PATENT DOCUMENTS

| 3,279,996 | 10/1966 | Long, Jr. et al. | 167/82 |
|---|---|---|---|
| 3,962,430 | 6/1976 | O'Neill | 424/185 |
| 4,819,661 | 4/1989 | Heil, Jr. et al. | 128/786 |
| 4,819,662 | 4/1989 | Heil, Jr. et al. | 128/786 |
| 5,041,107 | 8/1991 | Heil . | |
| 5,154,182 | 10/1992 | Moaddeb | 128/784 |
| 5,387,419 | 2/1995 | Levy et al. . | |
| 5,447,533 | 9/1995 | Vachon et al. | 607/120 |
| 5,531,780 | 7/1996 | Vachon | 607/120 |

FOREIGN PATENT DOCUMENTS

| 19705229 | 2/1997 | (DE) . |
| 2240721 | 8/1991 | (GB) . |
| 98/34653 | 2/1998 | (WO) . |

OTHER PUBLICATIONS

Bayston, R., et al., "Antimicrobial Activity of Silicon Rubber Used in Hydrocephalus Shunts, After Impregnation with Antimicrobial Substances", *J. Clin Pathol*, vol. 198, No. 134, 1057–1062, (Mar. 11, 1981).

Folkman, J., et al., "Drug Pacemakers in the Treatment of Heart Block", *Annals New York Acad. Sci.*, vol. 111, 857–858, (Jun. 11, 1964).

Labhasetwar, V., et al., "Epicardial Administration of Ibutilide from Polyurethane Matrices: Effects on Defibrillation Threshhold and Electrophysiologic Parameters", *J. Cardiovas. Pharm.*, vol. 24, 826–840, (1994).

Sintov, A., et al., "Drug Delivery Polyurethane as Myocardial Implant for Antiarrhythmic Therapy", *Proc. Intern. Symp. Cont. Rel. Bioact. Mater.*, vol. 14, 257–258, (1987).

Stokes, K., et al., "Drug Eluting Electrodes—Improved Pacemaker Performance", *IEEE Trans. Biomed. Eng.*, vol. BME–29, No. 8, 614, (Aug. 1982).

Stokes, K., et al., "Epicardial Lead Having Low Threshold, Low Polarization Myocardial Electrode", *Statutory Invention Reg. No. US H356*, (Nov. 3, 1987).

*Primary Examiner*—Carlos A. Azpuru
(74) *Attorney, Agent, or Firm*—Schwegman, Lundberg, Woessner & Kluth, P.A.

(57) ABSTRACT

Biologically active materials are provided in a cylindrical carrier medium with better control over the rate of delivery and length of time of delivery by providing a carrier having dissolved or dispersed therein at least two compounds having a common biologically active nucleus, but with different solubility parameters. The combination of the two different variants of the same drug with different solubility parameters provides the material with control over the rate of release of the compounds (by varying the proportions of the variants) and most importantly, extending the useful life of the device by enabling release of effective levels of the compounds over a longer period of time. The cylindrical carrier medium, comprised of silicone, further includes a tail, a skirt, or a rate-limiting membrane.

43 Claims, 5 Drawing Sheets

CONTROLLED RELEASE DRUG DELIVERY

RELATED APPLICATIONS

This patent application is a continuation-in-part of U.S. application Ser. No. 09/150,399, filed on Sep. 9, 1998, entitled "CONTROLLED RELEASE DRUG DELIVERY DEVICE", now abandoned, and is hereby incorporated by reference.

TECHNICAL FIELD

The present invention relates to natural and synthetic polymeric articles having chemical, biological, medicinal and/or physical or other active properties or combinations of properties. The invention also relates to methods for preparing such articles and delivering medication with such articles.

More specifically, the invention relates to body-implantable polymeric articles having active medicinal properties.

BACKGROUND

It is known in the art that active properties can be imparted to polymeric articles by a variety of methods. One common method is to incorporate one or more activating agents into the polymeric compound during the mixing or blending phase prior to processing or manufacturing the article. Activation is accomplished by thoroughly distributing the activating agents throughout the compounding ingredients. For example, synthetic thermoplastics, natural and synthetic rubbers and other polymeric materials have been blended with activating agents such as antibacterial, antistatic, electrically conductive and other chemically or physically active agents. The activated polymeric materials are then formed into sheets, fibers, rods or other configurations by molding, casting, extruding, calendering and/or other manufacturing or processing operations.

A second method widely used to impart certain active properties to the exposed or working surface is to apply a compound containing active agents to that surface. For example, anti-fouling marine paints, antifungal sprays and coatings, fire-resistant coatings and antistatic coatings have been applied to the surface of the article. The activity of such coating is superficially "skin deep" and surface activity is lost to the extent that the activated coating peels or is mechanically abraded, chipped or washed away from the inactive substrate. While this method affords certain flexibility in providing an activated surface, it is at best subject to severe limitations of available range of active ingredients that can be applied in this manner plus limited service life and efficiency.

Another method for the production of activated articles is to expose the article to the vapors of a volatilized chemical. This ancient technique has long been applied to textiles, polymer sheets, or the like and comprises vaporizing a volatile agent, usually a biologically active agent, and then exposing the textile or other article to the vapors. A major disadvantage of this method, however, is that it requires special buildings, ventilation and recovery equipment, and safety procedures. Since the active agent has a volatilization temperature which necessarily is much lower than the melting point of the article to which the activating vapors are applied, the activation may be readily lost where the article is exposed to elevated temperatures. Thus, the treated material may be rapidly deactivated when subjected to wet or dry heat, for example, by exposure to steam sterilization or other high temperature washing procedure, intense sunlight etc.

The use of controlled release implants for administering estradiol to ruminant animals has been described in U.S. Pat. No. 4,191,741. During implantation of such implants, conditions may be unsanitary, causing infections which could lead to loss of the implant. Use of an antibiotic or germicide layer, or a coating on the surface of the implant to reduce infections and to improve implant retention has been described in U.K. Patent No. 2 136 688 A. There an antibiotic coating facilitates parenteral administration of the implants under non-sterile conditions. Requirements for cleaning any implant needle, the site of implantation, and the implantation itself are minimized or reduced. Other infection-resistant implant materials have been described in the art, such as in U.S. Pat. No. 4,581,028 which describes infection-resistant materials suitable for use as vascular graft prostheses or other implanted devices.

It is known that antimicrobial agents can be layered or coated onto the surface of an implant to inhibit infection at the site of implantation. However, some difficulties have been encountered in implementing that technology. Surface-applied antimicrobial agents have been found to be easily dislocated from the surface of the implant by nominal mechanical activity on the implants, including during packaging. Loss of antimicrobial coating reduces the activity of the treatment significantly. Coating uniformity may also be difficult to control.

U.S. Pat. No. 3,857,934 provides a method for activating nonporous polymeric articles by applying the activating agents to one surface of the article so that the agents migrate throughout the body of the article and impart an effective level of activity throughout the article and on surfaces to which the activating agent has not been applied. The articles made by this method comprise an active layer which is applied on one surface of the article, and which contains an active migrating agent. The concentration of the agent is in excess of the concentration needed to provide an effective level of activity in the layer, and is sufficient, upon migration of the agent from the layer, to impart an effective level of activity throughout the entire article. The high concentration of the active migrating agent in the layer also provides a reservoir of activating material capable of replenishing the effective surface activity of the article.

The methods and products of U.S. Pat. No. 3,857,934 do not require extreme processing conditions so that volatile activating agents are conveniently used at normal temperatures; toxic agents can be handled safely; and a wide variety of inactive polymers can be given almost any desired activation. Only stocks of inactive articles are needed and the desired activation may be applied when desired. The activated article has long-lasting properties which persist even if a surface layer is removed and which are replenished from the reservoir of activating agent contained within the active layer.

U.S. Pat. No. 4,819,662 describes a device and a process for providing medical activity through introduced chemistry in a cardiac electrode. The invention comprises an implantable cardiac pacing lead including a porous platinum electrode, a flexible electrically conductive coil, and a crimp tube coupling the electrode to the distal end of the coil. There is a recess in the crimp tube, open to the electrode at the crimp distal tube end, which houses a matrix impregnated with a therapeutic drug. The electrode is highly porous and may be loaded with a therapeutic drug in liquid or solid form. The drug, because of its porous exposure to the environment, is immediately released upon implantation of the cardiac pacing device. A variety of different matrices carrying therapeutic drugs may be housed in the recess to provide elution of different drugs and at different rates.

U.S. Pat. No. 4,846,844 describes an improved antimicrobial implant coating comprising a silicone fluid in contact with the surface of the implant and a microbial agent in contact with the silicone fluid. The silicone fluid may be first applied to the implant and the antimicrobial agent may be applied to the fluid, for example as a dust applied to the liquid coating. The effectiveness of the application is asserted to derive from the high affinity of the silicone fluid to both the implant surface and to the antimicrobial agent.

SUMMARY

A material is described for delivering a chemically active, biologically active or medically active compound. The material comprises a solid carrier having at least two active compounds dissolved and/or dispersed therein. Each of the at least two active compounds are medically or biologically active compounds. Each of the at least two active compounds have an active nucleus which is common to each of the active compounds. The at least two active compounds also have maximum solubility levels in a single solvent which differ from each other. In one embodiment, the maximum solubility level of a first active compound in the solvent exceeds the maximum solubility level of a second active compound in the same solvent by at least approximately 10% by weight. In another embodiment, the maximum solubility level of a first active compound in the solvent exceeds the maximum solubility level of a second active compound in the same solvent by at least a factor of approximately two when measured as percent by weight. In a further embodiment, a first active compound is generally hydrophilic and a second active compound is generally hydrophobic. In yet another embodiment, a first active compound is generally soluble in the solvent and a second active compound is generally insoluble in the same solvent. Generally insoluble will be defined as having a saturation level in a solvent at the trace or marginal (e.g., less than about 1% by weight) levels.

The solid carrier often comprises biocompatible polymeric material. The solvent is preferably an aqueous solvent at approximately 37 degrees Centigrade. The solvents may, for example, comprise distilled, deionized water at 37 (or 37.2) degrees Centigrade, a standard saline solution at room temperature of 37 degrees Centigrade, or a bodily fluid (e.g., blood) at approximately 37 degrees Centigrade. The at least two (e.g., biologically) active compounds preferably comprise compounds having a common (e.g., biologically) active nucleus with each of said at least two (e.g., biologically) active compounds having different substituents groups thereon. The different substituent groups provide, at least in part, different solubility characteristics to the at least two (e.g., biologically) active compounds.

For example, the at least two medically active compounds may comprise compounds having a common medically active nucleus with each of said at least two medically active compounds having different substituents groups thereon. The different substituent groups may provide, at least in part, different solubility characteristics to the at least two medically active compounds.

A process for delivery of a biologically active ingredient to a patient is also described which comprises the steps of:
a) providing a material for delivering an (e.g., medically) active compound comprising a solid carrier material having dissolved and/or dispersed therein at least two (e.g., medically) active compounds, each of said at least two (e.g., medically) active compounds having an (e.g., medically) active nucleus which is common to each of the (e.g., medically) active compounds, and the at least two (e.g., medically) active compounds having maximum solubility levels in a solvent which differ from each other, and
b) implanting said material into a patient.

DETAILED DESCRIPTION

Figure 1:
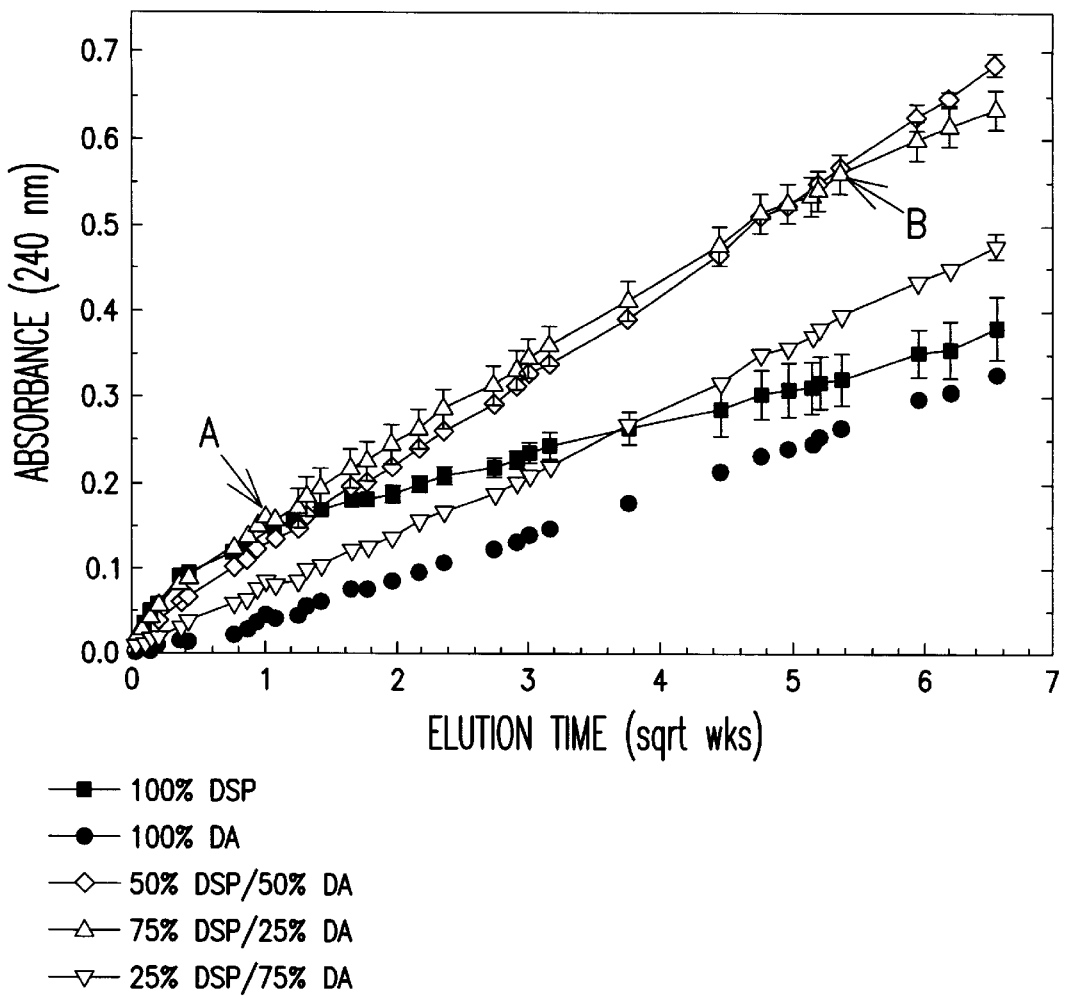
FIG. 1 shows a graphic representation of a Composite Matrix Elution Study for Release of Dexamethasone for a Silicone Rubber carrier polymer.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

The present invention relates to a solid carrier or carrying material having dissolved and/or dispersed therein at least two compounds having a chemical activity, such as a biologic activity, such as a therapeutic drug (steroid, antibiotic, stimulant, antiarrhythmic, depressant, antidepressant, fungistat, anti-inflammatory, inhibitor, etc.). The two compounds being present as at least two different forms of the same drug, said at least two different forms having different relative properties of hydrophilicity and hydrophobicity with respect to an aqueous environment, especially to either water, saline solutions or blood. It is preferred that this difference in physical properties be indicated by a measurable difference in solubility/dispersibility. In this way, comparing samples of the different forms of the same compound, one form will have solubility/dispersibility (preferably solubility) greater in a test liquid (e.g., purified/deionized water at 37 degrees C, a saline solution at 37 degrees C, or blood at average body temperature) than the solubility of the other compound in the same test liquid.

This difference in physical properties (and the chemical substituent means for obtaining it) should be a difference that does not significantly affect the therapeutic benefits or activity of the individual compound by any means. This does not imply that the therapeutic benefit or activity level of the individual compounds must be the same, but only that they further the same chemical activity. The difference in physical properties may be provided to the compounds by any known means and synthetic procedure, such as substitution with groups that provide the desired variations in solubility. For example, if the standard form of the compound is provided with an alkyl amine (or alkyl substituent on the nitrogen atom of a heterocyclic ring), the alkyl group may be provided with appropriate substituents to vary the solubility, such as groups with oleophilic or hydrophobic tendencies such as increased chain lengths or aromatic rings for increased oleophilicity, and hydrophilic groups such as sulfonate, carboxylic acid, etc. to increase the hydrophilicity of the individual compound. These techniques are well understood in the art, and are referred to in various fields as providing ballasting groups, solubilizing groups, insolubilizing groups, coupling groups, stabilizing groups, compatibility enhancing groups, and the like. Typical groups which are used to these effects include, but are not limited to hydrocarbon groups (such as aliphatic groups, aromatic groups, alkyl groups, allyl groups, aryl groups, phenyl groups, acyl groups, alkenyl groups, etc.), organic groups containing oxygen, nitrogen, sulfur or other elemental components (such as heterocyclic groups, aromatic compounds, ethers, esters, carboxylic acids, alcohols, sugars, starches, etc.), substituents on other groups or direct substitution of the fundamental central nucleus of the compound (i.e., the therapeutic drug), such substitutions, for example, including but not limited to amines, amino groups, aminoesters, sulfonates, sulfonic ester, sulfonyl groups, carboxylic acid groups, carboxylic ester groups, nitro, halogen (e.g., bromine, iodine, chlorine, fluorine), phosphonic acid, phosphoric acid, and the like. Each of these types of groups is known to have some influence on the relative solubility properties of various compounds.

The solubility altering structures of any specific compound or therapeutic nucleus should be selected primarily from the standpoint of convenience and expense of manufacture once the efficacy of the two variants of the same drug have been selected. The effect of the different substitution on the chemically effective core or nucleus is to provide the at least two active compounds with maximum solubility levels in a solvent which differ from each other.

Release characteristics of the at least one biologically active or medically active component from a carrier component into a surrounding medium can also depend upon the level of loading of the at least one active component. Loading levels can be below the saturation level of the at least one component in the polymeric carrier, at the saturation level of the at least one component in the polymeric carrier or above the at saturation level (e.g., supersaturation or overloading) of the least one component in the carrier. When loading is below the saturation limit of the at least one active component, the resultant active ingredient/carrier component matrix is referred to as a dissolved type matrix. Active ingredient release from this dissolved type matrix is dominated by diffusion of the active ingredient through a stable carrier material. Release of hydrophobic active ingredient forms into biological systems of a typically aqueous nature begin slowly. Thereafter, release can remain very slow, even perhaps at sub-therapeutic levels. This situation is clearly incompatible with the intent of a chronically implanted medical device. Alternatively, when active ingredient loading is above or greater than the saturation limit of that active ingredient in the carrier, the resultant active ingredient/carrier component matrix is referred to as a dispersed type matrix. Release of active ingredients from a dispersed type matrix occurs first at the matrix surface where surface bound drug is simply dissolved and released, leaving a cavity or porous structure. This cavity or porous structure, in turn, exposes deeper layers of active ingredient to the ingressing fluids of the surrounding medium resulting in dissolution and release of active ingredient. As this process continues over time, the active ingredient/carrier polymer matrix material assumes a more porous structure. Release of subsequently exposed internal layers of active ingredient requires that ingredient to diffuse through a porous and tortuous path to the exterior. Characteristics of porosity and tortuosity can be varied by varying, for example, active ingredient particle size. The release of hydrophilic active ingredient forms into biological systems of a typically aqueous nature begin very quickly and may become exhausted shortly after initial exposure to the external environment. Such systems may at best only provide short term therapy, clearly incompatible with the intent of certain long term implanted medical device. These systems may also be wasteful of drug. Rapidly releasing systems may be locally toxic to tissues.

It is contemplated in the practice of the present invention that the combination of the at least two forms of the biologically active ingredient or medically active ingredient in at least a single polymeric carrier can provide release of the active ingredient nucleus common to the at least two forms. The release of the active nucleus can be accomplished by, for example, enzymatic hydrolysis of the forms upon release from the carrier device. Further, the combination of the at least two forms of the biologically active ingredient or medically active ingredient in at least a single polymeric carrier can provide net active ingredient release characterized by the at least simple combination of the two matrix forms described above. This point is illustrated in FIG. 1 which compares the in vitro release of dexamethasone from matrices containing various fractions of two forms of the synthetic steroid dexamethasone, dexamethasone sodium phosphate (DSP; hydrophilic) and dexamethasone acetate (DA; hydrophobic). It is easy to see from these results that the release of dexamethasone acetate (specifically, 100% DA) is slower than all other matrices tested containing some degree or loading of dexamethasone sodium phosphate (hydrophilic). Still further, the resulting active ingredient release from the combined form matrix should be at least more rapid in the early stages of release than the slow single active ingredient component alone. Further still, the cumulative active ingredient release from the combined form matrix should be at least greater in the chronic stages than the fast single active ingredient component. Once again from FIG. 1, the two test matrices containing the greatest amount of dexamethasone sodium phosphate (specifically, 100% DSP, and 75% DSP/25% DA) began to slow in release as pointed out at points "A" and "B". And further still, the optimal therapeutic release can be designed through appropriate combination of the at least two active biological or medical ingredients in the polymeric carrier material. If as in this example, rapid initial release as well as continuous long tenn release is desired to achieve a therapeutic goal, the matrix composed of 50% DSP/50% DA would be selected.

This data is believed to show unexpected results in the practice of the present invention, at least in the following manner. The rate of release of both 100% systems of the two forms of Dexamethasone after sixteen (16) weeks ($t^{1/2}$=4 wks$^{1/2}$) were the lowest rates or total amounts of the drugs in the study. All combinations of the two forms of the drugs were released in greater amounts over time after four (4) months ($t^{1/2}=4$ $wks^{1/2}$) than either of the pure delivery systems. It is believed that one of ordinary skill in the art would have expected that the rate of delivery over time would have been primarily driven by the most soluble of the two forms, and that the rate of delivery of the most soluble form in the chosen solution would have been the approximately limiting rate of delivery. The data is quite surprising in its showing that all three combinations of the two forms of the drugs provided greater amounts of drug delivery over extended time frames (e.g., after more than sixteen weeks). This would not have been expected prior to the practice of the present invention.

It is also believed that this invention is based upon a generic physical effect amongst the two different forms of the drugs, a polymer, and a solution, and that this generic physical effect is not dependent upon the particular drug central nucleus or the particular polymer selected. As a physical property which has been proven for more than one drug system, it is believed that this effect now can be tailored for any combinations of physical variants of drugs in any pharmaceutically and/or biologically acceptable polymer carrier. This invention is believed to be applicable to any drug and any polymer which is acceptable to an animal body, or in any species of animal. The implications of this benefit is that many drug delivery systems may now be implanted with less frequent replacement required and that drugs which have not heretofore been implantably deliverable because of low release rates or short duration of release, may now be implantable. Polymer carriers such as polysiloxanes (whether rubbers, elastomers, or films), poly(meth)acrylic or polyacrylic resins, polyamide polymers, gelatin polymers (preferably crosslinked or hardened), polyurethanes, polyolefins, fluorinated polymers (e.g., polytetrafluoroethylene, Tedlar, Keflar, etc.), polyimides, and other biologically acceptable polymers (particularly those which are non-thrombogenic and non-immune responsive) are useful in the practice of the present invention.

Figure 2:
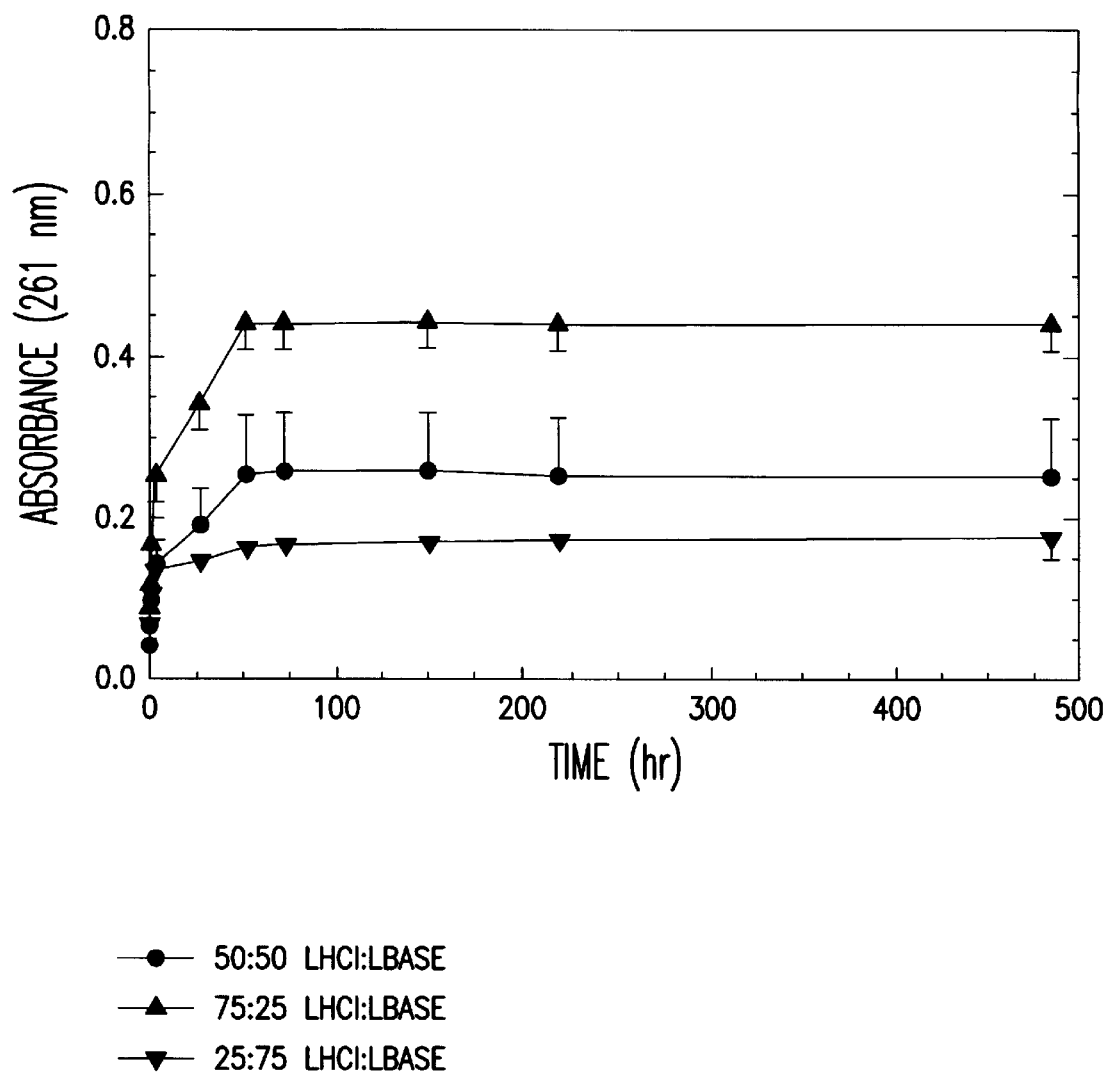
FIG. 2 shows a graphic representation of a Composite Matrix Elution Study for Release of Lidocaine for a Silicone Rubber carrier polymer.

Another example of release from a single carrier containing two forms of a single therapeutic nucleus is shown in FIG. 2. FIG. 2 shows the results of a Composite Matrix Elution Study for Lidocaine Release, using two different forms of Lidocaine. These results show the release of the antiarrhythmic agent lidocaine from silicone rubber. The load of drug in this short term study was arbitrarily chosen as 20%. It is known that the aqueous solubility of lidocaine base ("Base") is less than that of the lidocaine hydrochloride ("LHCl") salt. Consistent with the steroid release study illustrated earlier, the composite matrix containing the greatest water soluble fraction released more rapidly than the other matrices tested. In contrast to the steroid system described above, it can be readily observed that the matrix containing the greatest water soluble fraction released the greatest cumulative amount of lidocaine. The dramatic differences in rate release properties of the Lidocaine mixtures and the amount of Lidocaine released over time can be readily seen from the graph.

The benefit of the combination of the two different solubility variants of the same drug may be described as follows. It has been noted that when a single drug is provided from a matrix or carrier composition, the rate of drug delivery can change significantly over the life of the device. It is also desirable to provide a device wherein the effective level of delivery is as long as possible in time, particularly where drug delivery is prophylactic or long-term in application. That is, where a drug delivery system is to be provided on a relatively life-long or otherwise long term basis, it would be desirable for each individual device to itself have the longest term possible so that invasive procedures typically requiring expensive surgical procedures and mortality threat to a patient are minimized in frequency.

It has been found in the practice of the present invention that when two solubility variants of the same compound nucleus are provided within a carrier medium, even when there is a single carrier medium, that not only is the rate of delivery controllable by the combination of the two variants, but that in comparison to either variant being delivered alone, the length of time for effective delivery of a compound is extended when the variants are combined in a total weight amount which is the same as the total weight amount of the individual compounds. That is, when a standard carrier is used and there is a comparison of a) 1 gram of a hydrophilic variant, b) one gram of a hydrophobic variant, and c) a blend of 0.5 gram hydrophobic variant and 0.5 gram of hydrophilic variant (and other intermediate proportions, usually between 0.10–0.90 and 0.90–0.10 ratios), the blend of ingredients will provide an extended life of delivery of the compound when immersed in a liquid environment. Even when a hydrophilic compound carried in an insoluble binder (in a soluble binder, all material would be rapidly released) is used in an aqueous environment, where the maximum amount of compound would be expected to be leached out of the device during use, the combination or blend with the hydrophobic variant increases the life of effective delivery with respect to the single compound. This appears to be a physical phenomenon which is independent of the biologic or therapeutic activity of the drug. By balancing or optimizing the proportions of the at least two variants of the same drug within the delivery carrier, both the rate and length of time of delivery of effective amounts of the compounds can be controlled and optimized. The present invention therefore offers a simple and effective means of providing implanted or even transcutaneous delivery of drugs from a carrier medium in a cost-effective system that can maximize the length of time of delivery and rate of delivery without using mechanical means.

The invention as applied to biologically active products will be more fully appreciated in the light of the following examples.

The following problems are known to exist in tachyarrhythmia therapies: A) an inability to prevent the onset of atrial or ventricular arrhythmic events, B) an inability to provide painless, low energy, atrial or ventricular defibrillation therapy with known shock waveforms while maintaining adequate safety margins, C) the inability to provide long-term local drug delivery to a target organ such as the heart and D) a lack of a means to implant a device which can overcome these shortcomings. A first aspect of the invention outlined below is to provide a device or family of devices which will delay or completely prevent the onset of arrhythmic events in either or both chambers. A second concept is to provide a device which will effectively reduce defibrillation threshold requirements to levels that are approaching "painless" in character. A third concept is to provide a device which has sustained or otherwise long-term drug delivery capabilities. A fourth concept is to provide a "minimally invasive" surgical means to implant such a device upon or near the heart as the target organ.

Controlled released drug delivery for epicardial or endocardial therapies have been described variously over the years. In an epicardial therapy, it was first described by Folkman and Long in 1964 ("Drug Pacemakers in the Treatment of Heart Block", New York Acad. Sci., Jun. 11, 1964, p. 857). They described a wax or silicone rubber capsule technology capable of being loaded with candidate cardiac active agents. In open chest animal studies, a capsule was tunneled into the epicardial tissue. After being thus positioned, the capsule released its agent producing quantifiable effects on heart rate for four to five days. After this period of time, increased heart rate gradually returned to normal. In 1983, Stokes, et al. ("Drug Eluting Electrodes. Improved Pacemaker Performance", IEEE Trans. Biomed. Eng., Vol. BME-29, 1982, p. 614), described a steroid endocardial pacing electrode for purposes of reducing pacing thresholds. In 1987, Stokes, et al. ("Epicardial Lead Having Low Threshold. Low Polarization Myocardial Electrode", US H356, Nov. 3, 1987) described a myocardial pacing electrode with drug delivery capabilities. Although not specifically described, myocardial electrodes generally require a transchest surgical procedure in order to screw or in some fashion, impale the electrode into the heart tissue. Beginning in 1987, Levy's group at the University of Michigan (U.S. Pat. No. 5,387,419; PCT Appl. US 94/02838; and "Drug Delivery Polyurethane as Myocardial Implant for Antiarrhythmic Therapy", Proc. Intern. Symp. Cont. Rel. Bioact. Mat., Vol. 14, 1987, p. 257) described the acute effects of an epicardially positioned, polymeric drug loaded patch in induced ventricular tachycardia (VT) in open chest animal models. These studies showed the ability of these systems to convert induced VT to normal single rhythm (NSR) in the animal model. In 1994, Labhasetwar, et al. ("Epicardial Administration of Ibutilide rom Polyurethane Matrices: Effects on Defibrillation Threshold and Electrophysiologic Parameters", J. Cardiovasc. Pharm., Vol. 24, 1994, pp. 826–840), first described the reduction of defibrillation thresholds using epicardially positioned patch containing ibutilide in the acute canine model. In 1992, Moaddeb (U.S. Pat. No. 5,154,182) described an implantable, patch electrode, capable of delivering a drug, which is ". . . surgically attached . . . " to the epicardium. Such devices would be expected to release a candidate substance into the epicardial space for purposes such as reducing defibrillation threshold, and reducing inflammation.

Each of the previously cited technologies incorporate the controlled release of a candidate agent from a cardiac electrode positioned adjacent to the heart. Endocardially positioned devices may, in some cases, be restricted in drug loading due to obvious size limitations. Although epicardially positioned devices have the luxury of greater physical extent, they suffer because considerable surgical intervention is needed at implantation to accomplish direct application of the device. In view of these cited limitations, it is at least desirable to provide a device which can provide epicardial drug delivery for arrhythmia prevention and therapy in some manner which reduces the frequency of replacement of the device without significantly increasing the size of the device.

The present invention also relates to attached drug delivery matrices of a basically cylindrical design. The term "attached drug delivery systems" refers to devices having one particular functional use, such as a pacing device, electrical stimulating device or defibrillator, and having a drug delivery system attached thereto, the drug which is being released having either a primary (e.g., supporting the function) or a secondary (an effect independent of the function) relationship to the device. Also described are techniques with which the implantation of such devices or independent drug delivery matrices may be accomplished.

Figure 3:
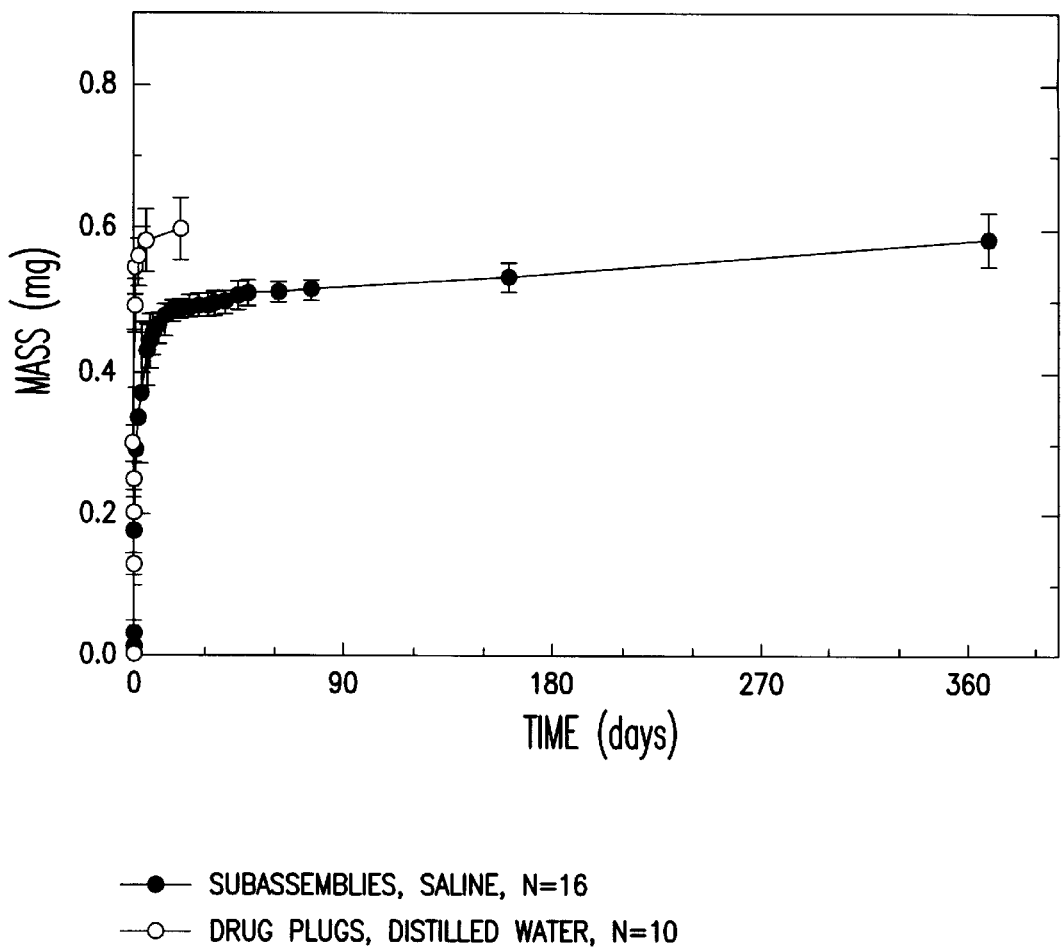
FIG. 3 shows a graphic representation of data for Dexamethasone Sodium Phosphate Release.

Regarding the drug delivery matrices, general matrix compositions are highly variable. Typically, as noted above, an inert, polymeric binder is used to hold or otherwise contain a candidate medication in a desired chemical state and desired physical shape. Some manufacturers have largely concentrated upon the use of polydimethylsiloxane (silicone), polyurethanes, polyamides, polyimides, and polyesters as the inert, non-biodegradable, binder material. Other materials have been reported, some of which may be or may not be biodegradable upon implantation. The drug substance contained within the binding material typically is a single, well known substance, previously characterized for its medical effects. According to the present invention, protracted, high-efficiency release of a drug substance (which may be referred to herein as a drug nucleus, common nucleus, drug family or family) can be accomplished by appropriate selection of the drug form, by mixing drug forms, in addition to or independent of covering or encapsulating a matrix in an impermeable capsule or covering. Combinations of these techniques would be anticipated to have cumulative effects on sustaining release. FIGS. 1 and 3 illustrate the prolonging effects on release. FIG. 1 summarizes the release of a family of two forms of dexamethasone (12% loading) having a common dexamethasone nucleus from cylindrical matrices. The two forms of this steroid used were dexamethasone sodium phosphate (DSP) and dexamethasone acetate (DA.). Three combinations of these forms were also investigated: 25% DSP/75% DA; 50% DSP/50 DA; and 75% DSP/25% DA. It can be seen that initially, the matrices which contained the greater fractions of the water-soluble steroid form of the nucleus, DSP, released greater amounts of the drug. It also demonstrates the converse for the hydrophobic form the drug. FIG. 1 also shows that release of the steroid forms is still observable after two years. FIG. 3 shows the effect of containment upon the release of DSP from cylindrical matrices. Here, the uncontained matrices released the DSP at a faster rate than the same matrices contained within a metallic capsule provided with an opening to accomplish drug release.

Contemplated implantation techniques for these devices may take two approaches. A first approach positions the drug delivery device within the pericardial space through the use of a puncture wound. It is desirable to use surgical techniques which allow access to the pericardial for purposes of relieving fluid build up, etc., where a small wound exposes the pericardium. Following dissection of the pericardium, a drug delivery matrix, as described further below, is inserted into the space. After allowing for a certain degree of positioning, if necessary, the wound is closed.

A second approach involves the use of a ". . . minimally invasive . . . " defibrillation lead implantation procedure, which includes using a modified endocardial lead implantation technique. A number of catheter and guide wire manipulations are performed to perforate the free wall of, for example, a right heart chamber, preferably the low pressure right atrium. Once breached, a generally cylindrical device, as further described below, is advanced into the pericardial space. For the instant purpose, this technique would be useful to position a long-term drug delivery system directly upon the myocardial surface for delivery of the desired agent(s).

Figure 4A:
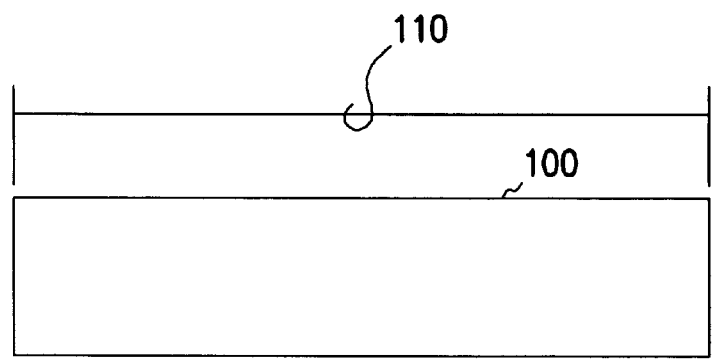
FIG. 4A illustrates a side view of a drug delivery device made in accordance with one embodiment.
Figure 4B:
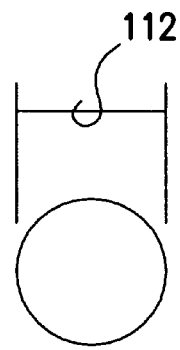
FIG. 4B illustrates an end view of a drug delivery device made in accordance with one embodiment.

Various embodiments of a drug delivery device loaded with the above described compositions are illustrated in FIGS. 4A–8. These drug delivery devices facilitate the long-term release of the drug compositions, and allow placement by the above techniques. FIGS. 4A and 4B illustrate one embodiment of a drug delivery device 100. The drug delivery device 100 is formed of a polymeric binder, such as silicone and is loaded with the drug compositions discussed above. For instance, the drug delivery device 100 includes a first compound of dexamethasone sodium phosphate and a second compound of dexamethasone acetate loaded therein. In another embodiment, the drug delivery device 100 includes 75% of a first compound of dexamethasone sodium phosphate and 25% of a second compound of dexamethasone acetate loaded therein. In another embodiment, the drug delivery device 100 includes 25% of a first compound of dexamethasone sodium phosphate and 75% of a second compound of dexamethasone acetate loaded therein. In yet another embodiment, the drug delivery device 100 includes 50% of a first compound of dexamethasone sodium phosphate and 50% of a second compound of dexamethasone acetate loaded therein. In a further embodiment, the drug delivery device 100 includes a first compound of lidocaine base and a second compound of lidocaine hydrochloride. In a still further embodiment, the drug delivery device 100 includes a first and second compound having an efficacy in tachyarrhythmia therapy. The drug delivery device 100 is adapted for long term release of the drug compositions. In one embodiment, the drug delivery device 100 has a cylindrical shape, and has a length 110 of 2–10 centimeters. In another embodiment, the drug delivery device 100 has a diameter 112 of 2–5 millimeters. Structures outside of these ranges may be used as medically prescribed. Smaller sizes, for example, may be necessary in intraparenchymal procedures and implants.

Figure 5:
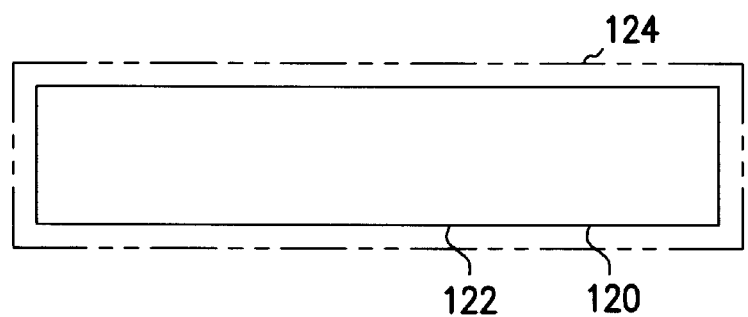
FIG. 5 illustrates a side view of a drug delivery device made in accordance with another embodiment.

FIG. 5 illustrates another embodiment of a drug delivery device 120. The drug delivery device 120 comprises a cylinder 122, for example, or otherwise suitable base shape, which is formed of a biocompatible material. The cylinder 122 is loaded with the drug compositions discussed above, and is adapted for long term release of the drug compositions. The drug delivery device 120 further includes a rate limiting membrane 124 disposed thereon. The rate limiting membrane 124, in one embodiment, fully encapsulates the cylinder 122.

Figure 6:
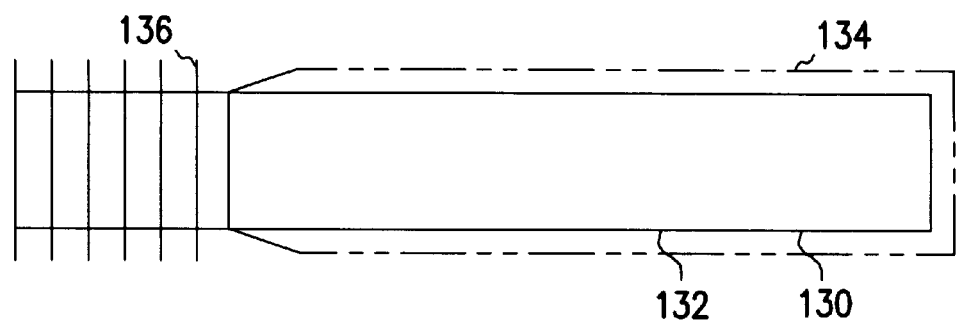
FIG. 6 illustrates a side view of a drug delivery device made in accordance with one embodiment.

FIG. 6 illustrates another embodiment of a drug delivery device 130. The drug delivery device 130 generally has a cylindrical shape 132, for example, or otherwise suitable base shape, which is formed of a biocompatible material such as silicone. The cylinder 132 is loaded with the drug compositions discussed above, and is adapted for long term release of the drug compositions. The drug delivery device 130 further includes a rate limiting membrane 134 disposed around at least a portion of the cylindrical shape 132. The drug delivery device 130 further includes a skirt 136 which is textured to assist in the attachment of the drug delivery device 130 to tissue once it is implanted. In one embodiment, the skirt 136 is formed of DACRON material. The skirt 136 advantageously encourages coagulation and tissue in-growth.

Figure 7:
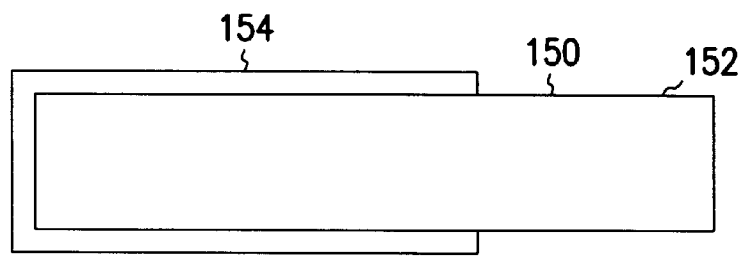
FIG. 7 illustrates a side view of a drug delivery device made in accordance with one embodiment.

In yet another embodiment, as illustrated in FIG. 7, a drug delivery device 150 is adapted for long-term release of drug compositions discussed above, where the drug delivery device 150 includes a rapid release portion and a sustained release portion. The drug delivery device 150 generally has a cylindrical shape 152, for example, or otherwise suitable base shape, which is formed of a biocompatible material such as silicone. The cylinder 152 is loaded with the drug compositions discussed above, and is adapted for long term release of the drug compositions. The drug delivery device 150, in one embodiment, further includes a rate limiting membrane 154 disposed around only a portion of the cylindrical shape 152. In another embodiment, the sustained release portion of the drug delivery device 150 is provided by masking or encapsulating the cylindrical shape 152 with material which interferes with or prevents the release of the drug compositions therefrom.

Figure 8:
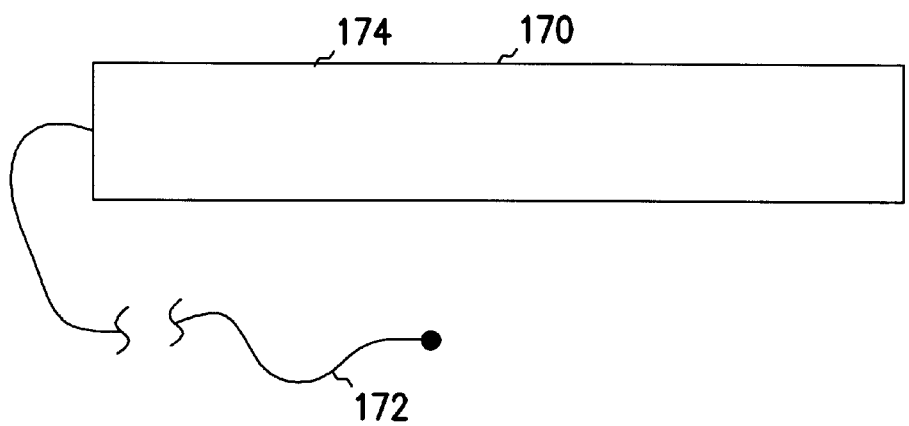
FIG. 8 illustrates a side view of a drug delivery device made in accordance with one embodiment.

In another embodiment, as illustrated in FIG. 8 a drug delivery device 170 is adapted for long-term release of the drug compositions discussed above. The drug delivery device 170 generally has a cylindrical shape 174, for example, or otherwise suitable base shape, which is formed of a biocompatible material such as silicone. The cylinder 174 is loaded with the drug compositions discussed above, and is adapted for long term release of the drug compositions. The drug delivery device 170, in one embodiment, further includes a tail 172, such as a suture-like tail. The tail 172 assists in retrieval of the drug delivery device 170 after it has been implanted. The tail 172 can be grasped for repositioning or removal and exchange of the drug delivery device 170. Furthermore, the tail 172 may be formed of a material which is identifiable by x-ray.

It is also contemplated at this time that a hybrid drug delivery-electrode device would allow both electrical stimulation and long-term drug delivery. The distal end of this hybrid device would be advanced through free wall opening and the proximal end would appropriately be connected to the pulse generating device.

This invention could also link pharmacological intervention with device intervention for purposes of delaying or preventing the onset of arrhymic events. Further, this invention would provide a means to reduce defibrillation threshold energy requirements to the pain-tolerable, or preferably painless character. Still further, this invention would provide long-term drug delivery to the heart as a target organ. Finally, this invention describes devices which are compatible with implant techniques considered to be minimally invasive.

There are a number of unique attributes to the practice of the present invention, in addition to its fundamental improvement and control in the rate, extent and percentage of drug/compound delivery. For example, it has been noted that where the two related compounds are distinctly hydrophilic/hydrophobic as between the two species, the two drugs may be carried in two distinct manners within the polymer matrix. The two species in a hydrophobic matrix (e.g., within the silicone polymers) could and have been shown to be carried as 1) a dissolved species (e.g., the hydrophobic species compatible with the polymer) and 2) a dispersed species (e.g., the hydrophilic species incompatible with the polymer). There may be some carryover of one species with the other in the dissolved or dispersed form, but each drug will comprise the majority of the drug/compound in any one form.

The mechanism for the delivery of the dispersed drug in combination with the dissolved drug is also thought to be unique. For example, where the dissolved drug/compound is hydrophobic and the dispersed drug is hydrophilic in a hydrophobic binder such as the silicone resins, the following method of delivery is believed to occur. Water vapor or other molecular form of water is believed to migrate through the silicone resin (which is known to be penetrable by water vapor). The water is absorbed by the hydrophilic dispersed particles of the compound. The absorption of the water causes the dispersed compound, which is confined by the polymer, to swell. As the swelling increases with additionally absorbed water, the polymer surrounding the dispersed particles is stressed, and has been seen to crack under the expansion pressures.

A liquid or paste phase of the particles in water may form within the polymer, and adjoining particles may join in a rivulet through fractured polymer which previously separated the two dispersed particles. One non-limiting hypothesis for the mechanism of operation of the system of the present invention is that the hydrophilic drug, being released in a soluble form into the fluid medium, leaves a cavity in the polymer. This cavity structure is composed of hydrophobic drug dissolved (solid state solution) in the polymer. The cavity may have a relatively large surface area in contact with the fluid medium, allowing the hydrophobic drug to also be released.

The system of the present invention also provides significant potential for improved transcutaneous delivery of compounds. In that environment, the compounds must often pass through at least two different interfaces, such as from the containing section (in this case the polymer matrix), through the adhesive, and then into the skin and vessels. Some of these interfaces may vary from hydrophilic to hydrophobic materials. By having the mixture of hydrophilic/hydrophobic compounds together in the practice of the present invention, the driving forces across the various interfaces can handle any combination, hydrophilic/hydrophilic, hydrophilic/hydrophobic, hydrophobic/hydrophilic, and hydrophobic/hydrophobic. The presence of both materials can assure a greater likelihood of transfer across any interfaces which might be encountered.

The delivery system has been emphasized for medical delivery systems, especially in vivo delivery systems. The delivery system assists in preventing or delaying the onset of arrhythmic events by the long-term release. The delivery techniques and materials may be used for other systems as well.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed:

1. A material for delivering a biologically active compound comprising a solid carrier material having dissolved and/or dispersed therein at least two biologically active compounds, each of said at least two biologically active compounds having a biologically active nucleus which is common to each of the biologically active compounds, and the at least two biologically active compounds having maximum solubility levels in a single solvent which differ from each other by at least 10% by weight; wherein said solid carrier comprises a biocompatible polymeric material.

2. A material for delivering a medically active compound comprising a solid carrier material having dissolved and/or dispersed therein at least two medically active compounds, each of said at least two medically active compounds having a medically active nucleus which is common to each of the medically active compounds, and the at least two medically active compounds having maximum solubility levels in a single solvent which differ from each other by at least 10% by weight; wherein said solid carrier comprises a biocompatible polymeric material.

3. The material of claim 1 wherein said solvent comprises distilled, deionized water at 37 degrees Centigrade.

4. The material of claim 2 wherein said solvent comprises distilled, deionized water at 37 degrees Centigrade.

5. The material of claim 2 wherein said solvent comprises a bodily fluid at 37 degrees Centigrade.

6. The material of claim 1 wherein the at least two biologically active compounds comprise compounds having a common biologically active nucleus with each of said at least two biologically active compounds having different substituents groups thereon, the different substituent groups providing, at least in part, different solubility characteristics to the at least two biologically active compounds.

7. The material of claim 2 wherein the at least two medically active compounds comprise compounds having a common medically active nucleus with each of said at least two medically active compounds having different substituents groups thereon, the different substituent groups providing, at least in part, different solubility characteristics to the at least two medically active compounds.

8. The material of claim 2 wherein the at least two medically active compounds comprise compounds having a common medically active nucleus with each of said at least two medically active compounds having different substituents groups thereon, the different substituent groups providing, at least in part, different solubility characteristics to the at least two medically active compounds.

9. The material of claim 4 wherein the at least two medically active compounds comprise compounds having a common medically active nucleus with each of said at least two medically active compounds having different substituents groups thereon, the different substituent groups providing, at least in part, different solubility characteristics to the at least two medically active compounds.

10. A process for delivery of a biologically active ingredient to a patient comprising:

providing an article for delivering a medically active compound comprising a solid carrier material having dissolved and/or dispersed therein at least two medically active compounds, wherein said solid carrier comprises a biocompatible polymeric material, each of said at least two medically active compounds having a medically active nucleus which is common to each of the medically active compounds, and the at least two medically active compounds having maximum solubility levels in a single solvent which differ from each other by at least 10% by weight, and implanting said article into a patient.

11. The process of claim 10 wherein said biologically active ingredient is a medically active ingredient.

12. The process of claim 10 wherein said solvent comprises distilled, deionized water at 37 degrees Centigrade.

13. The process of claim 11 wherein said solvent comprises a bodily fluid at 37 degrees Centigrade.

14. The process of claim 12 wherein the at least two medically active compounds comprise compounds having a common biologically active nucleus with each of said at least two medically active compounds having different substituent groups thereon, the different substituent groups providing, at least in part, different solubility characteristics to the at least two medically active compounds.

15. The process of claim 11 wherein the at least two medically active compounds comprise compounds having a common medically active nucleus with each of said at least two medically active compounds having different substituents groups thereon, the different substituent groups providing, at least in part, different solubility characteristics to the at least two medically active compounds.

16. A surgically implantable device having attached thereto the material of claim 2.

17. A drug delivery device comprising:

a solid carrier material having loaded therein at least two medically active compounds, each of said at least two medically active compounds having a medically active nucleus which is common to each of the medically active compounds, and the at least two medically active compounds having maximum solubility levels in a single solvent which differ from each other by at least 10% by weight; and the solid carrier comprising a cylinder formed of a biocompatible polymeric material.

18. The drug delivery device as recited in claim 17, further comprising a rate limiting membrane disposed on a portion of the cylinder.

19. The drug delivery device as recited in claim 17, wherein the cylinder is fully encapsulated by a rate limiting membrane.

20. The drug delivery device as recited in claim 17, wherein the carrier has a rapid release portion and a sustained release portion.

21. The drug delivery device as recited in claim 17, further comprising a tail coupled with a portion of the cylinder.

22. The drug delivery device as recited in claim 21, wherein the tail is formed of a material which is identifiable by x-ray.

23. The drug delivery device as recited in claim 17, wherein the cylinder has a length of 2–10 centimeters.

24. The drug delivery device as recited in claim 17, wherein the cylinder has a diameter of 2–5 millimeters.

25. The drug delivery device as recited in claim 17, further comprising a skirt coupled with the cylinder.

26. The drug delivery device as recited in claim 17, wherein a first compound comprises dexamethasone sodium phosphate (DSP), and a second compound comprises dexamethasone acetate (DA).

27. The drug delivery device as recited in claim 26, wherein the carrier has about 75% DSP and about 25% DA.

28. The drug delivery device as recited in claim 26, wherein the carrier has about 25% DSP and about 75% DA.

29. The drug delivery device as recited in claim 26, wherein the carrier has about 50% DSP and about 50% DA.

30. The drug delivery device as recited in claim 17, wherein the solid carrier is formed of silicone.

31. A drug delivery device comprising:

a solid carrier material having loaded therein at least two medically active compounds, each of said at least two medically active compounds having a medically active nucleus which is common to each of the medically active compounds, and the at least two medically active compounds having maximum solubility levels in a single solvent which differ from each other by at least 10% by weight;

a first medically active compound comprising dexamethasone sodium phosphate (DSP), and a second medically active compound comprises dexamethasone acetate (DA);

the solid carrier comprising a cylinder formed of a biocompatible polymeric material including silicone, the carrier having a rate limiting membrane disposed on at least a portion of the cylinder; and the cylinder having a length of 2–10 centimeters, and a diameter of 2–5 millimeters.

32. A drug delivery device comprising:

a solid carrier material of biocompatible polymeric material, the solid carrier material having loaded therein at least two medically active compounds, each of said at least two medically active compounds having a medically active nucleus which is common to each of the medically active compounds, and the at least two medically active compounds having maximum solubility levels in a single solvent which differ from each other by at least a factor of approximately two when measured as percent by weight.

33. The drug delivery device as recited in claim 32, wherein the at least two medically active compounds have an efficacy in tachyarrhythmia therapy.

34. A drug delivery device comprising:

a solid carrier material of biocompatible polymeric material, the solid carrier material having loaded therein at least two medically active compounds, each of said at least two medically active compounds having a medically active nucleus which is common to each of the medically active compounds;

wherein a first medically active compound is generally hydrophilic and a second medically active compound is generally hydrophobic.

35. A drug delivery device comprising:

a solid carrier material of biocompatible polymeric material, the solid carrier material having loaded therein at least two medically active compounds, each of said at least two medically active compounds having a medically active nucleus which is common to each of the medically active compounds;

wherein a first medically active compound is generally soluble in an aqueous solvent and a second medically active compound is generally insoluble in the aqueous solvent.

36. The drug delivery device as recited in claim 35, wherein the aqueous solvent is a bodily fluid at approximately 37 degrees Centigrade.

37. The drug delivery device as recited in claim 35, wherein the at least two medically active compounds have an efficacy in tachyarrhythmia therapy.

38. A process for delivering a medically active nucleus to a patient comprising:

implanting an article into the patient, wherein the article comprises a solid carrier material of biocompatible polymeric material, the solid carrier material having loaded therein at least two medically active compounds, each of said at least two medically active compounds having the medically active nucleus, and the at least two medically active compounds having maximum solubility levels in a bodily fluid which differ from each other by at least 10% by weight.

39. The process as recited in claim 38, wherein the bodily fluid is blood at approximately 37 degrees Centigrade.

40. The process as recited in claim 38, wherein the medically active nucleus has an efficacy in tachyarrhythmia therapy.

41. A process for delivering a medically active nucleus to a patient comprising:

implanting an article into the patient, wherein the article comprises a solid carrier material of biocompatible polymeric material, the solid carrier material having loaded therein at least two medically active compounds, each of said at least two medically active compounds having the medically active nucleus, and the at least two medically active compounds having maximum solubility levels in a bodily fluid which differ from each other by at least a factor of approximately two when measured as percent by weight.

42. A process for delivering a medically active nucleus to a patient comprising:

implanting an article into the patient, wherein the article comprises a solid carrier material of biocompatible polymeric material, the solid carrier material having loaded therein at least two medically active compounds, each of said at least two medically active compounds having the medically active nucleus, wherein a first medically active compound is generally hydrophilic and a second medically active compound is generally hydrophobic.

43. A process for delivering a medically active nucleus to a patient comprising:

implanting an article into the patient, wherein the article comprises a solid carrier material of biocompatible polymeric material, the solid carrier material having loaded therein at least two medically active compounds, each of said at least two medically active compounds having the medically active nucleus, wherein a first medically active compound is generally soluble in a bodily fluid and a second medically active compound is generally insoluble in the bodily fluid.

* * * * *

UNITED STATES PATENT AND TRADEMARK OFFICE
CERTIFICATE OF CORRECTION

PATENT NO.   : 6,168,801 B1
DATED        : January 2, 2001
INVENTOR(S)  : Ronald W. Heil, Jr. et al.

It is certified that error appears in the above-identified patent and that said Letters Patent is hereby corrected as shown below:

Title page,
Inventors, delete "KenKnight" and insert -- Kenknight --, therefor.

Related U.S. Application Data, delete "Continuation" and insert
-- Continuation-in-part --, therefor.

Column 5,
Line 53, insert -- at -- between "the" and "least".

Column 6,
Line 20, delete "device" and insert -- devices --, therefor.

Column 10,
Line 26, delete "DSP/50 DA" and insert -- DSP/50% DA --, therefor.
Line 30, insert -- of -- between "form" and "the".

Column 14,
Line 47, delete "claim 12" and insert -- claim 10 --, therefor.

Signed and Sealed this

Sixteenth Day of October, 2001

Attest:

*Nicholas P. Godici*

NICHOLAS P. GODICI
*Attesting Officer*   *Acting Director of the United States Patent and Trademark Office*